US008552166B2

(12) United States Patent
Tanner et al.

(10) Patent No.: US 8,552,166 B2
(45) Date of Patent: Oct. 8, 2013

(54) HIGH-AFFINITY NUCLEIC ACID APTAMERS AGAINST SCLEROSTIN PROTEIN

(75) Inventors: Julian Alexander Tanner, Hong Kong (CN); Ka-To Shum, Hong Kong (CN); Sze-Lai Celine Chan, Hong Kong (CN)

(73) Assignee: The University of Hong Kong, Hong Kong (HK)

(*) Notice: Subject to any disclaimer, the term of this patent is extended or adjusted under 35 U.S.C. 154(b) by 0 days.

(21) Appl. No.: 13/116,244

(22) Filed: May 26, 2011

(65) Prior Publication Data
US 2011/0294872 A1 Dec. 1, 2011

Related U.S. Application Data

(60) Provisional application No. 61/349,058, filed on May 27, 2010.

(51) Int. Cl.
C07H 21/04 (2006.01)

(52) U.S. Cl.
USPC ... 536/23.1; 536/24.3; 536/24.31; 536/24.33; 536/24.5

(58) Field of Classification Search
None
See application file for complete search history.

(56) References Cited

U.S. PATENT DOCUMENTS
2009/0286743 A1* 11/2009 Miller et al. .................... 514/14

FOREIGN PATENT DOCUMENTS
WO WO 2008/141129 A1 * 11/2008

OTHER PUBLICATIONS

Brunkow, Mary E., "Bone Dysplasia Sclerosteosis Results from Loss of the SOST Gene Product, a Novel Cystine Knot-Containing Protein", Am. J. Hum. Genet., 68, 2001, pp. 557-589.
Balemans, Wendy, et al., "Increased bone density in sclerosteosis is due to the deficiency of a novel secreted protein (SOST)", Human Molecular Genetics, 2001, No. 5, vol. 10, pp. 537-543.
Boyden, Lynn M., et al., "High Bone Density Due to a Mutation in LDL-Receptor-Related Protein 5", The New England Journal of Medicine, vol. 346, No. 20, pp. 1513-1521.
Choi, Mei Y., et al., "Biochemical consequences of sedlin mutations that cause spondyloepiphyseal dysplasia tarda", Biochem J., 2009, 423, pp. 233-242.
Ellington, Andrew D., et al., "In Vitro selection of RNA molecules that bind specific ligands", Nature, vol. 346, 1990, pp. 818-822.
Goltzman, David, "Discoveries, Drugs and Skeletal Disorders", Nature Reviews, 2002, vol. 1, pp. 784-796.
Gong, Y., et al., "LDL Receptor-Related Protein 5(LRP5) Affects Bone Accrual and Eye Development", Cell, vol. 107, 2001, pp. 513-523.
Hamersma, H., "The natural history of sclerosteosis", Clinical Genetics, 2003, 63, pp. 192-197.
Harada, Shun-ichi, et al., "Control of osteoblast function and regulation of bone mass", Nature, vol. 423, 2003, pp. 349-355.
Larkin, M.A., et al., "Sequence Analysis", Bioinformatics, vol. 23, No. 21, 2007, pp. 2947-2948.

(Continued)

*Primary Examiner* — Amy Bowman
(74) *Attorney, Agent, or Firm* — Turocy & Watson, LLP

(57) ABSTRACT

Described are nucleic acid aptamers that are able to bind to and inhibit the function of sclerostin, which is an important negative regulator of bone growth. The aptamers have application as therapeutics for diseases of bone including osteoporosis, osteopenia, osteoarthritis and other osteoporosis-related conditions and complications.

12 Claims, 7 Drawing Sheets

(56) References Cited

OTHER PUBLICATIONS

Li, X., et al., "Sclerostin Antibody Treatment Increases Bone Formation, Bone Mass, and Bone Strength in a Rat Model of Postmenopausal Osteoporosis", Journal of Bone and Mineral Research, vol. 24, No. 4, 2009, pp. 578-588.

Li, X. et al "Sclerostin Binds to LRP5/6 and Antagonizes Canonical Wnt Signaling", Journal of Biomedical Chemistry, vol. 280, No. 20, Issue of May 20, 2005, pp. 19883-19887.

Murphy, Michael B., et al., "An improved method for the in vitro evolution of aptamers and applications in protein detection and purification", Nucleic Acids Research, 2003, vol. 31, No. 18, pp. 1-8.

Nimjee, Shahid, et al., "Aptamers: An Emerging Class of Therapeutics", Annu. Rev. Med., 2005, 56, pp. 555-583.

Que-Gewirth, et al., "Gene therapy progress and prospects: RNA aptamers", Gene Therapy, 2007, 14, pp. 283-291.

Rey, Jean-Phillippe, et al., "Wnt Modulators in the Biotech Pipeline", Developmental Dynamics, 239, 2010, pp. 102-114.

Semenov, Michael, et al., "SOST Is a Ligand for LRP5/LRP6 and a Wnt Signaling Inhibitor", The Journal of Biomedical Chemistry, vol. 280, No. 29, 2005, pp. 26770-26775.

Shafer, Richard H., et al., "Biological Aspects of DNA/RNA Quadruplexes", Nucleic Acid Sci, 56, 2001, pp. 209-227.

Shum, Ka To, et al., "Differential Inhibitory Activities and Stabilization of DNA Aptamers against the *SARS coronavirus* Helicase", ChemBioChem, 2008, 9, pp. 3037-3045.

Shum, Ka To., et al., "Identification of a DNA aptamer that inhibits sclerostin's antagonistic effect on Wnt signalling", Biochem. J. 2011, 434, pp. 403-501.

Tuerk, Craig, et al., "Systematic Evolution of Ligands by Exponential Enrichment: RNA Ligands to Bacteriophage T4 DNA Polymerase", Research Articles, www.sciencemag.org, 2011, pp. 505-249.

Veverka, Vaclav, et al., "Characterization of the Structural Features and Interactions of Sclerostin", The Journal of Biological Chemistry vol. 284, No. 16, pp. 10890-10900.

K.T. Shum, et al., "Identification of a DNA aptamer that inhibits sclerostin's antagonistic effect on Wnt signalling", Biochem. J. (2011), 434, pp. 493-501.

* cited by examiner

| Aptamer clone | Core region of the aptamer sequences (5' to 3') | No. of nucleotides | Percentage |
|---|---|---|---|
| Scl 1 | GTTTCCAAAGCCGGGGGGGTGGGATGGGTT------------ | 30 | 55% |
| Scl 2 | TTGCGCGTTAATTGGGGGGGTGGGTGGGTT------------ | 30 | 24% |
| Scl 3 | TGCCTTGTTATTGTGGTGGGCGGGTGGGAC------------ | 30 | 7% |
| Scl 4 | ----------GGGGGGGGTGGGGTGGGTCAATATTCTCGTC | 31 | 3% |
| Scl 5 | TTGCGCGTTAATTGGGGGGGTGGGTGGGTT------------ | 30 | 3% |
| Scl 6 | CCCTCCAAAGCGGGGGGGGTGGG-TGGGCAG----------- | 30 | 3% |
| Scl 7 | TTCTGTCACATGTGGGGGGGGGGGTGGGTT------------ | 30 | 3% |

SEQUENCE LISTING

<160> NUMBER OF SEQ ID NOS: 14

<210> SEQ ID NO 1
<211> LENGTH: 14
<212> TYPE: DNA
<213> ORGANISM: Artificial Sequence
<220> FEATURE:
<223> OTHER INFORMATION: Artificially synthesized nucleotide sequence
<220> FEATURE:
<221> NAME/KEY: misc_feature
<222> LOCATION: (3)..(3)
<223> OTHER INFORMATION: n is any nucleotide residue
<220> FEATURE:

```
<221> NAME/KEY: misc_feature
<222> LOCATION: (6)..(7)
<223> OTHER INFORMATION: n is any nucleotide residue
<220> FEATURE:
<221> NAME/KEY: misc_feature
<222> LOCATION: (10)..(10)
<223> OTHER INFORMATION: X is any nucleotide residue
<220> FEATURE:
<221> NAME/KEY: misc_feature
<222> LOCATION: (10)..(10)
<223> OTHER INFORMATION: n is any nucleotide residue

<400> SEQUENCE: 1
ggnggnnggn tggg                                                               14

<210> SEQ ID NO 2
<211> LENGTH: 30
<212> TYPE: DNA
<213> ORGANISM: Artificial Sequence
<220> FEATURE:
<223> OTHER INFORMATION: Artificially synthesized nucleotide sequence

<400> SEQUENCE: 2
gtttccaaag ccggggggt gggatgggtt                                               30

<210> SEQ ID NO 3
<211> LENGTH: 30
<212> TYPE: DNA
<213> ORGANISM: Artificial Sequence
<220> FEATURE:
<223> OTHER INFORMATION: Artificially synthesized nucleotide sequence

<400> SEQUENCE: 3
ttgcgcgtta attgggggg tgggtgggtt                                               30

<210> SEQ ID NO 4
<211> LENGTH: 30
<212> TYPE: DNA
<213> ORGANISM: Artificial Sequence
<220> FEATURE:
<223> OTHER INFORMATION: Artificially synthesized nucleotide sequence

<400> SEQUENCE: 4
tgccttgtta ttgtggtggg cgggtgggac                                              30

<210> SEQ ID NO 5
<211> LENGTH: 31
<212> TYPE: DNA
<213> ORGANISM: Artificial Sequence
<220> FEATURE:
<223> OTHER INFORMATION: Artificially synthesized nucleotide sequence

<400> SEQUENCE: 5 gggggggtg ggtgggtca atattctcgt c                                              31

<210> SEQ ID NO 6
<211> LENGTH: 30
<212> TYPE: DNA
<213> ORGANISM: Artificial Sequence
<220> FEATURE:
<223> OTHER INFORMATION: Artificially synthesized nucleotide sequence

<400> SEQUENCE: 6
ttgcgcgtta attgggggg tgggtgggtt                                               30

<210> SEQ ID NO 7
<211> LENGTH: 30
<212> TYPE: DNA
```

```
<213> ORGANISM: Artificial Sequence
<220> FEATURE:
<223> OTHER INFORMATION: Artificially synthesized nucleotide

<400> SEQUENCE: 7
ccctccaaag cggggggggt gggtgggcag                                    30

<210> SEQ ID NO 8
<211> LENGTH: 30
<212> TYPE: DNA
<213> ORGANISM: Artificial Sequence
<220> FEATURE:
<223> OTHER INFORMATION: Artificially synthesized nucleotide sequence

<400> SEQUENCE: 8
ccctccaaag cggggggggt gggtgggcag                                    30

<210> SEQ ID NO 9
<211> LENGTH: 38
<212> TYPE: DNA
<213> ORGANISM: Mus musculus

<400> SEQUENCE: 9
gtatgtatga attcatgcat gcagccctca ctagcccc                           38

<210> SEQ ID NO 10
<211> LENGTH: 34
<212> TYPE: DNA
<213> ORGANISM: Mus musculus

<400> SEQUENCE: 10
gtatgtatct cgagctagta ggcgttctcc agct                               34

<210> SEQ ID NO 11
<211> LENGTH: 64
<212> TYPE: DNA
<213> ORGANISM: Artificial Sequence
<220> FEATURE:
<223> OTHER INFORMATION: Artificially synthesized nucleotide sequence
<220> FEATURE:
<221> NAME/KEY: misc_feature
<222> LOCATION: (42)..(42)
<223> OTHER INFORMATION: n is a random sequence of 30 nucleotide
      residues

<400> SEQUENCE: 11
ccgtaatacg actcactata ggggagctcg gtaccgaatt cnaagctttg cagagaggat   60
cctt                                                                64

<210> SEQ ID NO 12
<211> LENGTH: 41
<212> TYPE: DNA
<213> ORGANISM: Artificial Sequence
<220> FEATURE:
<223> OTHER INFORMATION: Artificially synthesized nucleotide sequence

<400> SEQUENCE: 12
ccgtaatacg actcactata ggggagctcg gtaccgaatt c                       41

<210> SEQ ID NO 13
<211> LENGTH: 22
<212> TYPE: DNA
<213> ORGANISM: Artificial Sequence
<220> FEATURE:
<223> OTHER INFORMATION: Artificially synthesized nucleotide sequence

<400> SEQUENCE: 13
```

```
aaggatcctc tctgcaaagc tt                                          22

<210> SEQ ID NO 14
<211> LENGTH: 22
<212> TYPE: DNA
<213> ORGANISM: Artificial Sequence
<220> FEATURE:
<223> OTHER INFORMATION: Artificially synthesized nucleotide sequence

<400> SEQUENCE: 14
aagctttgca gagaggatcc tt                                          22
```

HIGH-AFFINITY NUCLEIC ACID APTAMERS AGAINST SCLEROSTIN PROTEIN

CROSS-REFERENCE TO RELATED APPLICATIONS

This application claims priority to provisional application Ser. No. 61/349,058, filed on May 27, 2010, which is incorporated herein by reference.

FIELD

Described herein are novel nucleic acid ligands (aptamers) directed against sclerostin, which is an extracellular negative regulator of bone growth. The disclosed aptamers have promise to directly stimulate bone formation and be used as therapeutics to treat bone disease such as osteoporosis.

BACKGROUND

Nucleic acid aptamers are in vitro evolved nucleic acids that are able to bind and inhibit protein function.

Nucleic acid aptamers have been developed over the last 20 years to develop therapeutic aptamers against a variety of targets for a number of diseases including macular degeneration, HIV, cancer, cardiovascular disease, amongst others. One aptamer, pegaptanib (MACUGEN), is used clinically for the treatment of macular degeneration, discovered by Gilead Sciences, licensed to Eyetech Pharmaceuticals and marketed outside the USA by Pfizer. Other aptamer based drugs are in clinical trials against coagulation factors, growth factors, inflammation markers and other targets. To our knowledge, no aptamers have been developed in relation to osteoporosis.

Osteoporosis has a significant medical and economic impact worldwide. In developed nations, approximately 4% of the population has osteoporosis, and the economic burden to the US alone has been estimated at $14 billion annually. Currently, the majority of pharmacological agents presently used in the clinic are bisphosphonate based antiresorptive agents, including alendronate (FOSAMAX), risedronate (ACTONEL) or ibandronate (BONIVA).

The established drug agents can be somewhat effective in controlling bone mass, but they have a number of disadvantages including poor oral absorption, esophagitis and osteonecrosis of the jaw. Therefore, there is a move toward anabolic agents that stimulate bone formation that would potentially accelerate bone growth. Recently, teriparatide (recombinant parathyroid hormone, FORTEO) was approved as the first anabolic agent to enter the clinic but there have been some concerns regarding FORTEO that it is only effective to remodel bone during the first 12 months treatment and then efficacy declines.

Sclerostin is an osteocyte-specific negative regulator of bone formation which makes it an attractive drug target for osteoporosis therapy. Amgen is developing protein-based antibodies against sclerostin for osteoporosis therapy (Human Clinical Phase 2). Novartis and Eli Lily are also developing sclerostin-blocking antibodies (Preclinical). OsteogeneX is developing small molecule inhibitors against sclerostin, currently in preclinical and lead optimization.

Antibodies generally have a number of limitations including risk of immune response, batch to batch variation and limited shelf-life. Small molecules have significant problems of binding affinity and specificity.

SUMMARY

The present invention provides aptamers, including their formulations and/or compositions, that bind to the protein sclerostin, referred to herein as "sclerostin aptamers", and methods for using such sclerostin aptamers for the treatment and prevention of osteoporosis and other related bone diseases.

The invention provides for an alternative molecular approach that stimulates bone growth by inhibiting sclerostin function and that has fewer side effects for osteoporosis and other related diseases. This is addressed with the development of nucleic acid aptamers that target and inhibit sclerostin specifically and effectively. This invention specifically relates to aptamers that are able to bind to and inhibit the function of sclerostin, which is an important negative regulator of bone growth and implicated in bone disease such as osteoporosis. This invention claims aptamers, as a unique new composition of matter, that inhibit sclerostin function and have clear implications as therapeutics for osteoporosis and related diseases.

The present invention is directed to methods of using anti-sclerostin aptamers as therapeutics for stimulating bone formation. The method comprises administering to a human an amount of anti-sclerostin aptamers that is effective to cause an increase in the rate of bone formation.

The formulations described herein comprise a sclerostin aptamer or a pharmaceutically acceptable salt thereof The formulations may comprise any aptamer that binds to sclerostin or a variant or a fragment thereof Preferably, the aptamer binds to sclerostin and inhibits its activity.

The present invention also provides methods of using anti-sclerostin aptamer for treating bone-related diseases, disorders or conditions wherein the presence of sclerostin causes undesirable pathological effects. Such diseases, disorders and conditions include but not limited to osteoporosis, osteopenia, osteoarthritis, osteomalacia, osteodystrophy, osteomyeloma, bone fracture, Paget's disease, osteogenesis imperfecta, bone sclerosis, aplastic bone disorder, humoral hypercalcemic myeloma, multiple myeloma, and bone thinning following a disorder that causes or induces bone thinning. Such bone thinning diseases, disorders and conditions include but not limited to metastasis, hypercalcemia, chronic renal disease, kidney dialysis, primary hyperparathyroidism, secondary hyperparathyroidism, inflammatory bowel disease, Crohn's disease, long-term use of corticosteroids, or long-term use of gonadotropin releasing hormone (GnRH) agonists or antagonists. Subjects may be male or female of any ages.

The present invention may administer to a human subject an amount of anti-sclerostin aptamers alone or in combination with other drugs.

The present invention also provides diagnostic methods of quantifying expression of sclerostin. The anti-sclerostin aptamers may be labeled by a detectable substance including but not limited to fluorescent materials, enzymes, luminescent materials and radioactive materials. Such embodiments of the invention can be used to detect sclerostin levels in a biological sample.

BRIEF DESCRIPTION OF THE DRAWINGS

FIG. 2 is a table showing the sequences of the aptamers that were isolated from the ssDNA pool after 15 rounds of selection against sclerostin and are claimed in this invention. Conserved nucleotides are marked by asterisk.

DETAILED DESCRIPTION

The invention will now be described further with reference to the following experimental procedures and results. The following experimental details are intended to be exemplary of the practice of the present invention, and should not be construed to limit the scope of the invention in anyway.

Figure 1:
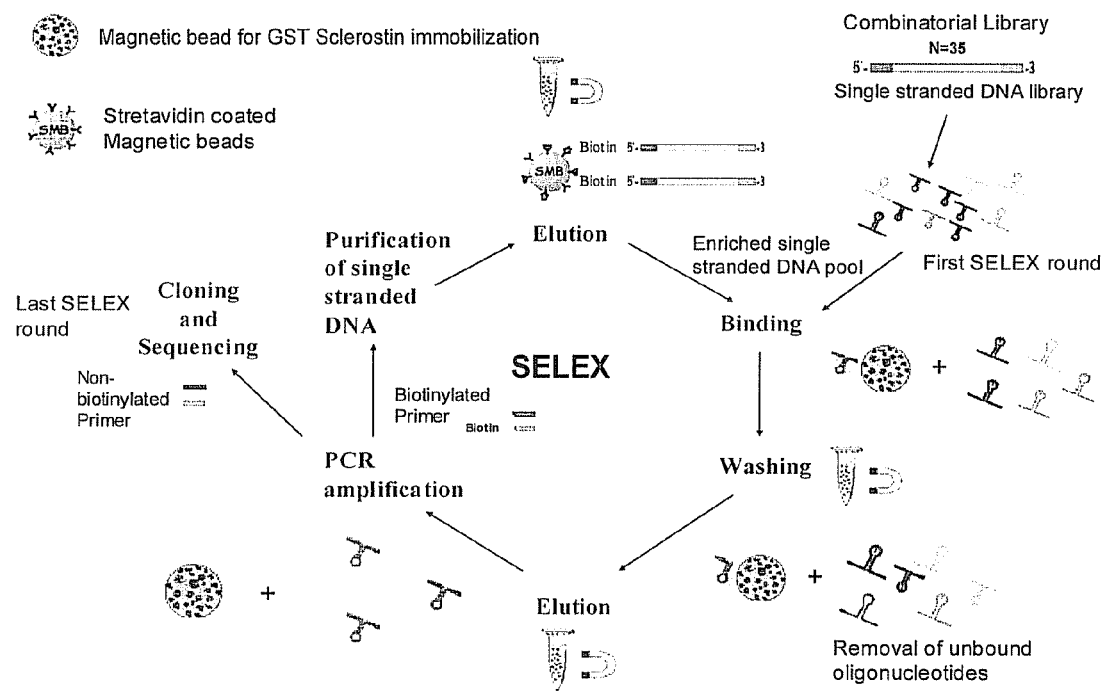
FIG. 1 is a drawing showing the method used for sclerostin aptamer selection.

Seven different sequences of DNA aptamers were identified and claimed in this invention with details in FIG. 2 using the scheme in FIG. 1. Notably, aptamer Scl 1 and Scl 2 were a dominant sequence that accounted for 79% total in the pool. In addition, high level of sequence homology was observed, with a conserved motif present in almost all clones at approximately the same location in the random region (5'-GGXG-GXXGGXTGGG-3') (SEQ ID NO: 1), where X is any nucleotide base.

Figure 3:
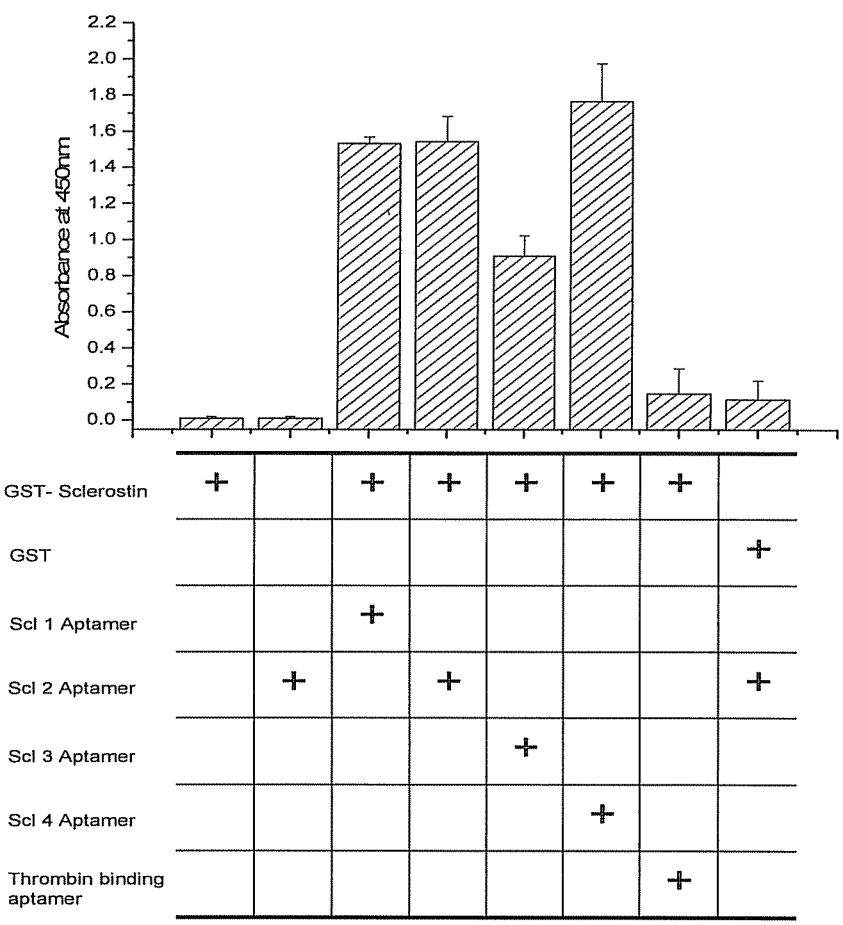
FIG. 3 is a graph showing determination of relative binding strength of aptamers against sclerostin using an aptamer enzyme-linked assay. Combinations of sclerostin aptamers, thrombin binding aptamers, GST-Sclerostin and GST protein (indicated by plus signs below the graph) were evaluated for their binding activity and cross-reactivity. The data are averaged from triplicate samples.

Enzyme-linked binding assay showed specific binding of sclerostin aptamers to sclerostin. The results suggest that their relative binding strength for sclerostin were in the following order: Scl4>Scl 1=Scl 2>Scl 3 (FIG. 3). Aptamers showed negligible binding to GST, suggesting that the aptamers bound specifically to sclerostin. In addition, a thrombin binding aptamer with authentic G-quadruplex structure did not cross-react with the sclerostin protein.

Figure 4:
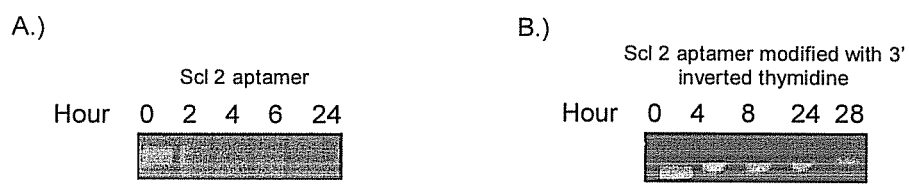
FIG. 4 is a drawing showing the stability of modified aptamers: A.) unmodified Scl 2 aptamers and B.) 3' inverted thymidine modified Scl 2 aptamers evaluated in MC3T3-E1 cells that were supplemented with 5% FBS.

Sclerostin aptamers were stabilized by capping the 3' end with 3' inverted thymidine (3'-InT) and evaluated in MC3T3-E1 cells that were supplemented with 5% FBS (FIG. 4). Without any modifications, aptamers was quickly degraded by nuclease in serum as noted by the smear. In the case of 3' inverted thymidine aptamer, the oligo remained intact for 28 hr, suggesting that the stability of aptamers can be greatly enhanced.

Several different kinds of modifications can also be made to the aptamers to reduce exonuclease degradation and increase lifetime in the serum of an individual. Degradation can occur with intramuscular, intravenous and oral administration of the aptamer. Modification of the 3' end of the aptamer with inverted thymidine, deoxythymidine nucleotide, and polyethylene glycol (PEG) can reduce degradation of the oligonucleotide aptamer increases stability of the aptamer. In one embodiment, PEG has an average molecular weight from about 20 to 80 kDa.

Further, the phosphodiester linkages of the deoxyribose-phosphate backbone of the aptamer can also be modified to improve stability. As used through this document, the term "aptamer" refers to a molecule having repeating units of the structure shown in Formula 1. Wavy lines demarcate one nucleotide and/or repeat unit from a neighboring nucleotide and/or repeat unit.

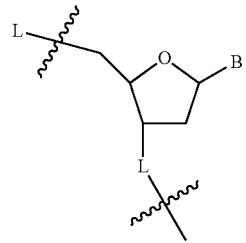

(1)

Each repeat unit of Formula 1 has a deoxyribose moiety linked to one of the common nucleotide bases (B): guanine, thymine, cytosine, adenine and/or uracil. The base (B) for each repeating unit is independent from the other repeat units. The nucleotide sequences disclosed herein describe the order of appearance of bases (B) in an aptamer from the repeat unit on the 5' end of the aptamer to the 3' end of the aptamer.

"L" is a linker group that links the deoxyribose moiety of adjacent repeat units. In the well-known structure of DNA, the L group is a phosphate group $PO_4H$, which can exist as a salt or in a neutral protonated form. The deoxyribose moiety together with the linker group forms the backbone of the aptamer, where the nucleotide base "B" varies independently barriers between repeat units. The majority of the linker groups (L) forming the repeat units of Formula 1 in the aptamer are phosphate groups. As such, a majority of the backbone of the aptamer can be referred to as a deoxyribose-phosphate backbone. Many nuclease enzymes exist that can degrade oligonucleotide molecules without specificity for the specific nucleotide base sequence of the oligonucleotide molecule. Without wishing to be bound by any one particular theory, linker groups "L" other than phosphate can be incorporated into an oligonucleotide or aptamer to prevent degradation by nucleases.

In one embodiment, L can be replaced with a group as shown in Formula 2, where $X_{1-4}$ are independently O or S. $X_2$ and $X_3$ can be bonded to either the 3' carbon or the 5' carbon of a deoxyribose moiety. In one embodiment, $X_1$ is O and $X_4$ is O that can be either protonated or unprotonated. In another embodiment, one or more of $X_1$ and/or $X_3$ is S and $X_1$ and $X_4$ are O, where O can be either protonated or unprotonated. Where one of $X_2$ and/or $X_3$ are S, the aptamer can be referred to as having a thioester linkage in the deoxyribose-phosphate backbone.

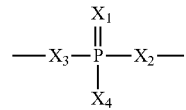

(2)

In another embodiment, the linker group "L" is an amide-containing group as shown in Formula 3, where R is one or more of hydrogen and a substituted or unsubstituted $C_1$-$C_{20}$ hydrocarbyl group. A hydrocarbyl group is a carbon containing group that is straight or branched, saturated or unsaturated, cyclic or non-cyclic, aromatic or non-aromatic, where with carbon can be bonded with 1 or more heteroatoms including O, N, S and halides. Where the linker group "L" is a group having Formula 3, the aptamer can be referred to as having an amide linkage in the deoxyribose-phosphate backbone. The "NR" group of Formula 3 can be bonded to either the 3' carbon or the 5' carbon of a deoxyribose moiety. In one embodiment, R is methoxymethyl or methoxyethyl.

$$-O-\overset{O}{\underset{OH}{\overset{\|}{P}}}-\overset{R}{N}- \quad (3)$$

In one embodiment, the aptamer has from about 20 to about 50 nucleotide bases and/or repeat units. In other embodiment, the aptamer has from about 14 to about 50 nucleotide bases and/or repeat units. In another embodiment, the aptamer has from about 30 to about 35 nucleotide bases and/or repeat units. In one embodiment, the aptamer has from about 1 to about 15 repeat units having a linker "L" selected from Formulae 2-3. In another embodiment, the aptamer has from about 1 to about 10 repeat units having a linker "L" selected from Formulae 2-3. In another embodiment, the aptamer has from about 1 to about 5 repeat units having a linker "L" selected from Formulae 2-3. In yet another embodiment, the aptamer has more than 10 repeat units having a linker "L" selected from Formulae 2-3. Linker groups in repeat units not selected from formulae 2-3 are phosphate In one embodiment, the aptamer has from about 10 to about 100% of the repeat units having a linker "L" selected from Formulae 2-3. In another embodiment, the aptamer has from about 10 to about 70% of the repeat units having a linker "L" selected from Formulae 2-3. In yet another embodiment, the aptamer has from about 10 to about 50% of the repeat units having a linker "L" selected from Formulae 2-3. In still another embodiment, the aptamer has from about 10 to about 30% of the repeat units having a linker "L" selected from Formulae 2-3. In a further embodiment, the aptamer has from about 10 to about 20% of the repeat units having a linker "L" selected from Formulae 2-3. Linker groups in repeat units not selected from formulae 2-5 are phosphate.

Many nucleases are exonucleases that degrade oligonucleotides from the 5' or 3' end. As such, in one embodiment a linker group L selected from Formula 2-3 is located within about 5 repeat units from the 5' or the 3' end of the apatmer. In another embodiment, a linker group L selected from Formula 2-3 is located within about 3 repeat units from the 5' or the 3' end of the apatmer. In yet another embodiment, a linker group L selected from Formula 2-3 is located is part of the repeat unit on the 5' or the 3' end of the apatmer.

Degradation of the aptamers can also be reduced by the inclusion of modified nucleotide bases (B). The pyrimidine nucleotide bases, cytosine, thymine and uracil can be replaced with alkylated pyrimidines. Examples of alkylated pyrimidines include pseudoisocytosine; N4,N4-ethanocytosine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; 1-methylpseudouracil; 3-methylcytosine; 5-methylcytosine; 5-methylaminomethyl uracil; 5-methoxy amino methyl-2-thiouracil; 5-methoxycarbonylmethyluracil; 5-methoxyuracil; uracil-5-oxyacetic acid methyl ester; psuedouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; 2-thiocytosine; 5-propyluracil; 5-propylcytosine; 5-ethyluracil; 5-ethylcytosine; 5-butyluracil; 5-pentyluracil; 5-pentylcytosine; methylpsuedouracil; and 1-methylcytosine. The purine nucleotide bases, adenine and guanine, can be replaced by alkylated purines. Examples alkylated purines include 8-hydroxy-N6-methyladenine; inosine; N6-isopentyl-adenine; 1-methyladenine; 1-methylguanine; 2,2-dimethylguanine; 2-methyladenine; 2-methylguanine; N6-methyladenine; 7-methylguanine; 2 methylthio-N6-isopentenyladenine; and 1-methylguanine.

Aptamer Sequences

An aptamer is an oligonucleotide that binds to a non-nucleic acid biological target. In a double-stranded DNA molecule, the nucleotide bases form intermolecular pyrimidine-purine pairs through the well-known Watson-Crick base paring. Aptamers are believed to recognize non-nucleic acid biological targets through bonding of the nucleotide bases with non-nucleic acid molecules. The aptamers can be single-stranded, double-stranded, or form intramolecular base-pairing in portions of the aptamer sequence.

Seven different aptamer sequences were identified as capable of binding to sclerostin:

```
                                      (SEQ ID NO: 2)
5'-GTTTCCAAAGCCGGGGGGGTGGGATGGGTT-3'
(Scl 1);

(SEQ ID NO: 3)
5'-TTGCGCGTTAATTGGGGGGTGGGTGGGTT-3'
(Scl 2)

(SEQ ID NO: 4)
5'-TGCCTTGTTATTGTGGTGGGCGGGTGGGAC-3'
(Scl 3);

(SEQ ID NO: 5)
5'-GGGGGGGGTGGGGTGGGTCAATATTCTCGTC-3'
(Scl 4);

(SEQ ID NO: 6)
5'-TTGCGCGTTAATTGGGGGGTGGGTGGGTT-3'
(Scl 5);

(SEQ ID NO: 7)
5'-CCCTCCAAAGCGGGGGGGTGGGTGGGCAG-3'
(Scl 6); and (SEQ ID NO: 8)
5'-TTCTGTCACATGTGGGGGGGGGGTGGGTT-3'
(Scl 7).
```

SEQ ID NOS: 2-8 all contain SEQ ID NO: 1 as a conserved sequence. In addition to SEQ ID NOS: 2-8, variants of SEQ ID NOS: 2-8 are also believed to have anti-sclerostin activity. The term "anti-sclerostin activity," "sclerostin inhibitor," "antagonist," "neutralizing," and "downregulating" refer to a compound (or its property, as appropriate) which acts as an inhibitor of sclerostin relative to sclerostin activity in the absence of the same inhibitor. The term "variant" refers to a polynucleotide or aptamer that differs in nucleotide sequence from a "parent" polynucleotide or aptamer by virtue of addition, deletion and/or substitution of one or more nucleotide bases in the parent sequence. A variant polynucleotide or aptamer possesses a similar or identical function to the parent polynucleotide or aptamer. A variant polynucleotide or aptamer has a similar nucleotide base sequence to a parent and satisfies at least one of the following: a polynucleotide or aptamer having a nucleotide base sequence that is one or more of at least about 40%, at least about 50%, at least about 60%, at least about 70%, at least about 80%, at least about 90%, at least about 95%, and at least about 98% identical. Identity with respect to SEQ ID NOS: 2-8 is defined herein as the percentage of nucleotide bases in a candidate or variant sequence that are identical with the parent sequence, after aligning the sequences to achieve the maximum percent sequence identity. None of 5'-terminal and/or additions shall be construed as affecting sequence identity nor shall the chemical linkage of the 3' or 5' end of any aptamer to a non-nucleotide group be construed as affecting sequence identity.

In one embodiment, a variant is an aptamer containing one of SEQ ID NO: 2-8 where additional nucleotide repeat units are inserted or added on the 5' or 3' end of the aptamer. In another embodiment, a variant is an aptamer containing one of SEQ ID NO: 2-8 where one or more pyrimidine nucleotide bases is substituted for another pyrimidine nucleotide base or a modified pyrimidine nucleotide base and/or one or more purine nucleotide bases is substituted for another purine nucleotide base or a modified purine nucleotide base.

Aptamer Properties

Figure 5:
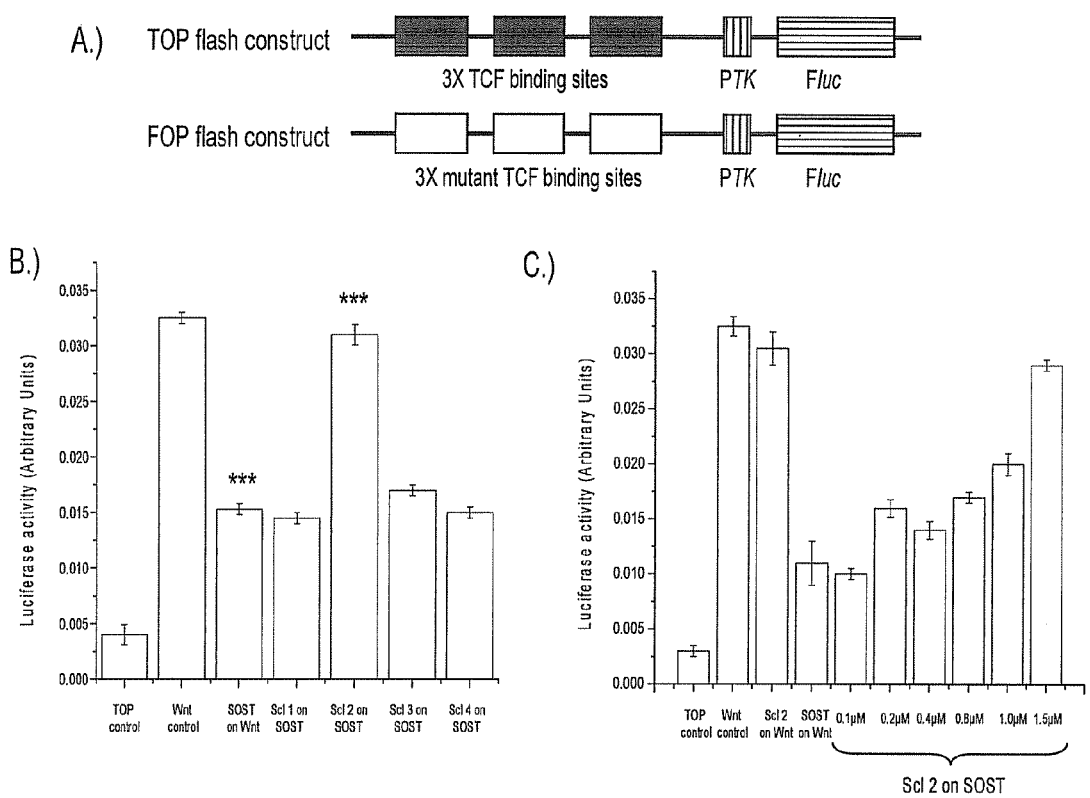
FIG. 5 is a drawing showing the principle of a Wnt reporter assay and the effect of the sclerostin aptamers in cell culture. A.) Schematic showing the principles behind the reporter luciferase activity assay. B.) Effect of 3 inverted thymidine modified sclerostin aptamers on Wnt3a mediated activity in MC3T3-E1 cells. Data shown represents triplicate values of independent assays. *** represents that values are statistically significant from each other analyzed by unpaired t-test with 95% confidence. C.) Effect of varying concentration of 3' inverted thymidine modified Scl 2 aptamers against Sclerostin functions.

Aptamers modified to be conjugated with inverted thymidine on the 3' end inhibit sclerostin function in cell culture. We employed lymphoid enhancer factor/T-cell factor (LEF/TCF) luciferase reporter assay to study the effects of aptamers on Wnt mediated activity in osteoblast MC3T3-E1 cells which is considered to be an in vitro model of bone development. Both LEF and TCF are nuclear transducers of an activated Wnt/β-catenin pathway as they interact with β-catenin (FIG. 5A).

To further investigate the modified aptamers, TOP flash luciferase reporter contains three Wnt-specific binding sites for TCF/LEF transcription factors and the firefly luciferase reporter (Fluc) under the control from herpex simplex virus thymidine kinase; whilst the FOP flash construct is identical to the TOP construct with three TCF binding sites that are mutated and thus serves as a negative control. The luciferase gene is driven by the promoter which is specifically activated by the binding of β-catenin through the activation of Wnt. We initially compared the 3' InT aptamers using Wnt-reporter assay (FIG. 5B).

Aptamer Scl 2 significantly inhibited sclerostin function in Wnt signaling, restoring the luciferase activity similar to the Wnt control. In the presence of Wnt, the signaling pathway is activated, having a large luciferase signal. Sclerostin is an antagonist of canonical Wnt signaling, binding to LRP5/6. So, the luciferase activity decreased. The efficacy of the aptamers was tested at fixed concentration at 1.5 µM.

To further study the effect of 3' InT aptamer Scl 2 against sclerostin's antagonistic effect on Wnt signaling, 3' InT aptamers Scl 2 was added in varying concentration from 0.1 µM to 1.5 µM. With increasing concentration, the aptamer specifically blunts the antagonistic effect of sclerostin against Wnt signaling. The inhibitory effects of aptamers can be saturated at 1.5 µM.

Figure 6:
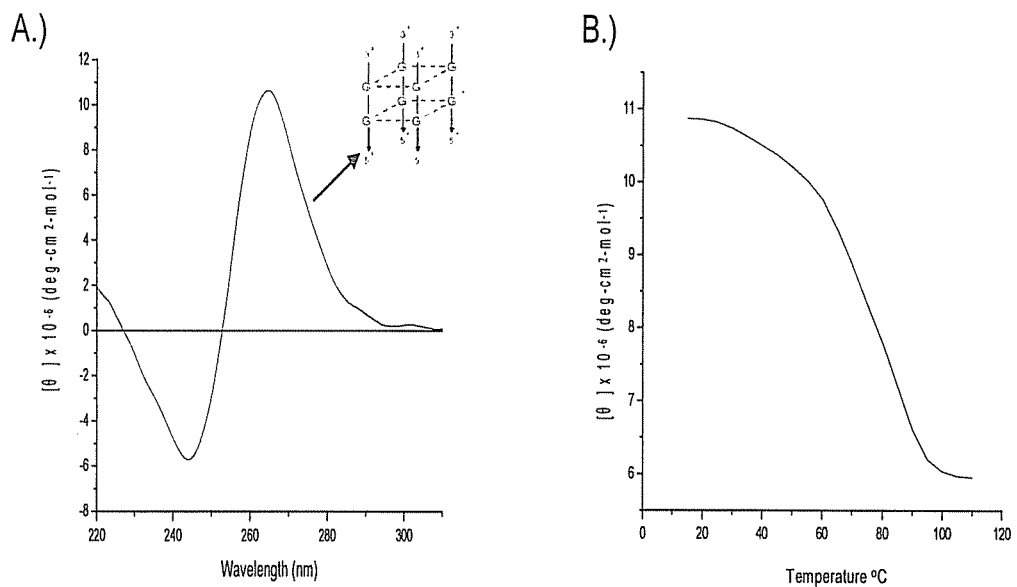
FIG. 6 is a graph determining the secondary structure of Scl 2 aptamers. A.) CD spectra of Scl 2 aptamers. B.) CD melting spectra of Scl 2 aptamers.

Biophysical properties of sclerostin aptamers were characterized by circular dichroism to experimentally demonstrate whether G-quadruplex structure was formed in the aptamer sequence. In their CD spectra, aptamer Scl 2 showed a positive maximum peak near 265 nm (FIG. 6A). This is a spectroscopic evidence of parallel G-quadruplex structure. Moreover, we determined the theimal stability of the G-quadruplex structure of aptamer Scl 2 by melting CD and showed that the $T_m$ value of aptamer Scl 2 is 75° C., suggesting that the structure is very stable that is suitable for potential therapeutic use in the cellular environment (FIG. 6B).

The G-quadruplex structure is a square arrangement of four guanine nucleotide bases. The four guanine nucleotide bases forming the G-quadruplex structure can come from one DNA aptamer strand or two or more DNA aptamer strands. That is, the G-quadruplex structure can be an intramolecular structure or an intermolecular structure.

Figure 7:
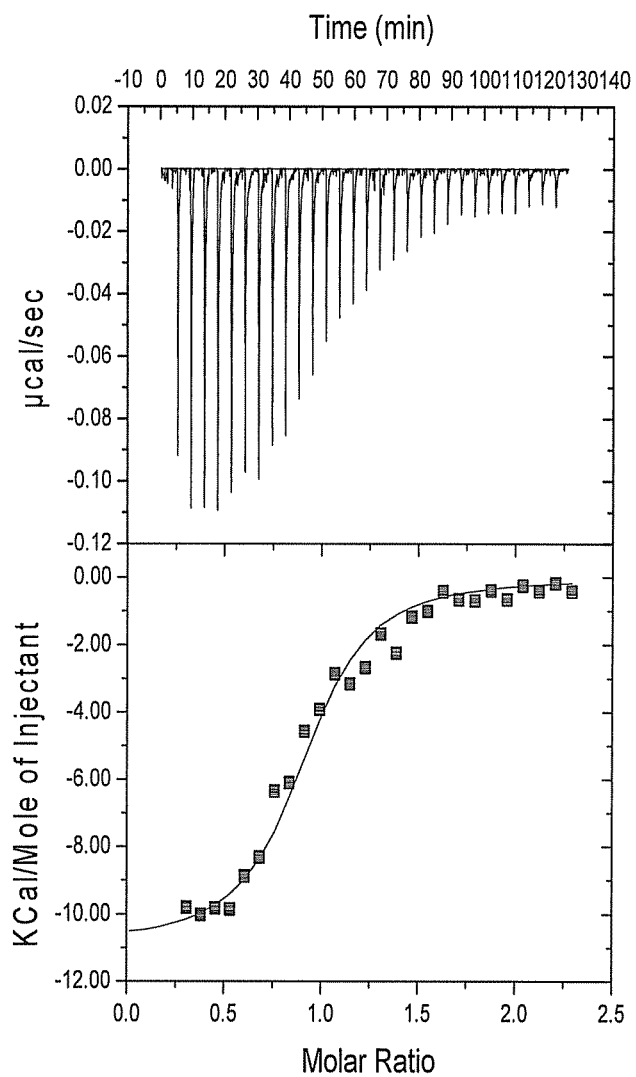
FIG. 7 is a graph showing data by Isothermal Titration calorimetry to measure the binding between sclerostin and sclerostin aptamers. Titration (top) of Scl 2 aptamer with serial injections of sclerostin. Binding isotherms (bottom) resulting from integration of raw calorimetric data after correction for the heat of aptamer dilution.

Sclerostin-aptamer interaction was investigated by studying the thermodynamics of the interaction of aptamer Scl 2 with sclerostin by Isothermal Titration Calorimetry. In the upper panel of FIG. 7 the calorimetric titrations of the aptamers into sclerostin solution conducted at 25° C. An exothermic heat pulse was observed after each injection of aptamers into the protein solution. The binding stoichiometry was fitted using simple single site binding model. Our results showed that the binding stoichiometry (n) of aptamer-protein complexes clearly indicates that in solution n=0.91±0.02 molecules of Scl 2 aptamer bind to one Sclerostin molecule. The dissociation constant for the interaction of aptamer Scl 2 with sclerostin is 500 nM that is a competitive value in DNA-protein interactions. In addition, the values of ΔH and ΔS reveal that the binding processes are enthalpically driven with a favorable enthalpy of reaction (ΔH) at 25° C. of −10.9 kcal/mol offset by an unfavorable entropy of reaction (TΔS=−2.3 kcal/mol).

While at least one embodiment of the present invention has been shown and described, it is to be understood that many changes and modifications may be made thereunto without departing from the philosophy and scope of the invention as defined in the appended claims.

Materials and Methods

The present invention describes aptamers that bind to sclerostin. Sclerostin was obtained by cloning cDNA of SOST obtained from Mus musculus 6 days neonate head cDNA. The coding region of SOST was amplified by PCR with the forward primer 5'-GTATGTATGAATTCATGCATGCAGC-CCTCACTAGCCCC-3' (SEQ ID NO: 9) and the reverse primer 5'-GTATGTATCTCGAGCTAGTAGGCGT-TCTCCAGCT-3' (SEQ ID NO: 10). The PCR product was gel purified, digested with EcoR1/XhoI and ligated with a similarly digested pGEX-4T1 vector to make the plasmid pGEX-SOST.

For heterologous expression of sclerostin, 2 liters of LB broth supplemented with ampilicin (50 µg/ml) were inoculated with saturated pGEX-SOST/BL21 (DE3) culture (1/200 dilution) and grown at 37° C. until $A_{600}$=0.6. Protein expression was induced by addition of isopropyl-1-thio-β-D-galactopyranoside (0.25 mM), and cultures were incubated at 25° C. for 4 h. After cooling to 4° C., the cells were harvested by centrifugation and resuspended in buffer A: phosphate buffer saline (PBS; pH7.3) with protease inhibitors, 1 g of wet cell pellet/5 ml of buffer.

For purification of sclerostin, cells were lysed by sonication and then centrifuged (30 min, 30,000×g), and the supernatant was filtered and then applied to 5 ml GSTrap HP columns. The 5-ml column was washed with 40 ml of buffer A, then 50 ml Buffer B (50 mM Tris-HCl, pH 8.0, 10 mM reduced glutathione (Calbiochem) to elute the protein. Pure fractions (by SDS-PAGE) were combined and stored at 4° C. for short term or frozen at −80° C. for long term storage.

Sclerostin aptamers were selected by magnetic separation using sclerostin immobilized on GST-magnetic beads. The starting point of the selection process was a random degenerate ssDNA library (SelexApt) that was chemically synthesized and HPLC purified. (SelexApt: 5'-CCG TAA TAC GAC TCA CTA TAG GGG AGC TCG GTA CCG AAT TC-(N30)-AAG CTT TGC AGA GAG GAT CCT T-3') (SEQ ID NO: 11). Another way of describing SEQ ID NO: 11 is that SEQ ID NO: 11 is SEQ ID NO: 12 coupled to SEQ ID NO: 14 with another sequence therebetween (the N30 sequence). Primers that anneal to the 5'- and 3'-sequences flanking the degenerate region of SelexApt used during the selection and cloning were: "SelexF", 5'-CCG TAA TAC GAC TCA CTA TAG GGG AGC TCG GTA CCG AAT TC-3' (SEQ ID NO: 12); "SelexR", 5'-AAG GAT CCT CTC TGC AAA GCT T-3' (SEQ ID NO: 13); in non-biotinylated and 5'-biotinylated forms, respectively (HPLC purified). 1 nmol of DNA library was incubated with GST-sclerostin immobilized on GST magnetic beads for 30 min at room temperature. The unbound DNA was separated and removed by washing with phosphate buffered saline (PBS). The bound sequences were eluted with 10 mM reduced glutathione (GSH) and PCR amplified using biotinylated primers. Single-stranded DNA pool was obtained by streptavidin-magnetic bead purification.

Iterations of 15 cycles were performed with counter selection against magnetic beads at rounds 3, 6, 9 and 12. During the last round of SELEX, the recovered DNA molecules were PCR amplified using non-biotinylated primers and cloned into pCR-Blunt II TOPO vectors (Invitrogen) and sequenced. Multiple sequence alignment was performed by clustalW2.

For aptamer-enzyme linked assays, 96 well plates prepacked with glutathione sepharose media (GE healthcare) were coated with 500 ng purified proteins (GST-sclerostin or GST) in 200 μl coating buffer (50 mM Tris-Cl pH 8.5, 100 mM NaCl and 100 mM KCl) for 1.5 hr at room temperature. The wells were washed 4 times with coating buffer. Biotinylated oligodeoxynucleotides (Scl 1, 2, 3, 4 aptamers, thrombin binding aptamer and oligodeoxynucleotide 35-mer random sequence) were heated to 90° C. and then cooled quickly to 4° C. 50 nM aptamers were incubated with protein in the 96 well plate overnight at 4° C. shaking gently. Wells were washed 6 times with 200 μl of coating buffer for each wash 10 min on a plate vortex. Streptavidin horseradish peroxidase was diluted 1:2000 in buffer and 200 μl aliquots applied to each well. Strips were incubated for 30 min at room temperature and washed againas described above. Then, 150 μl of Turbo-3,3',5,5'-tetramethylbenzidine (FMB) was added to each well and incubated for 20 min at room temperature in the dark. The reaction was quenched by addition of 150 μl of 1M $H_2SO_4$ and the protein bound aptamer-streptavidin complexes were quantified by determining the absorbance at 450 nm.

For T-cell factor luciferase reporter assays, MC3T3-E1 cells were seeded in 24-well plate and transiently transfected with either 100 ng of TOP-Wnt induced luciferase plasmid or FOP (control plasmid) using Lipofectamine reagent. Wnt3a (800 ng), Sclerostin (800 ng) expression vectors were co-transfected when needed. 10 ng of *Renilla luciferase* vector was co-transfected to correct for transfection efficiency. 6 hr post-transfection, medium were changed to antibiotics containing medium supplemented with appropriate amount of aptamers and incubated for 24 hr. Cells were lysed with 100 μl of passive lysis buffer and 20 μl was used for analyses. Luciferase assays were performed using a luciferase reporter system.

For aptamer stability assessment, 1 μM of Scl 2 and 3' inverted thymidine modified Scl 2 were added to MC3T3-E1 cells at 80% confluency. Cells were grown in 6 well plates and with 2 ml complete medium (α-MEM, supplemented with 5% FBS, penicillin/Streptomycin and fungizone) at 37° C. supplemented with 5% $CO_2$. At time points indicated, 10 μl of medium was loaded onto urea-PAGE and electrophoese. Gels were stained with 1:10000 SYBR Gold for 20 min and images observed under UV.

For Circular Dichroism, oligonucleotides (10 μM) were resuspended in Tris-HCl (10 mM, pH7.5) buffer that contained KCl (100 mM). Samples were heated at 90° C. for 5 min, followed by gradual cooling to room temperature. CD spectra were collected on a JASCO J810 spectropolarometer (JASCO, Md., USA) equipped with a water-jacketed cell holder at 310 nm-220 nm, by using 4 scans at 100 nm min$^{-1}$, 1 s response time, 1 nm bandwidth. Quartz cells with an optical path length of 1 mm were used for the measurement. The scans of the buffer alone were subtracted from the average scans for the sample. CD melting curves obtained at wavelength 260 nm allowed an estimation of melting temperature, Tm, the mid-point temperature of the unfolding process.

For Isothermal Titration Calorimetry, equilibrium binding studies between anti-sclerostin aptamers and scleorstin are performed on MicroCal VP-ITC. In a typical ITC experiment, 15 μM GST-sclerostin or 20 μM GST was loaded into the cell with 200 μM aptamer or random sequence in the titrating syringe. GST-sclerostin and GST were dialyzed into the PBS buffer with a MWCO of 10,000. The titration experiments were performed at 25° C. with an initial 0.2 μl injection, followed by thirty 1.2 μl A injections. The spacing between injections was 200 s. The stirring speed during the titration was 900 rpm. It should be understood that the examples and embodiments described herein are for illustrative purposes only and that various modifications or changes in light thereof will be suggested to persons skilled in the art and are to be included within the spirit and purview of this application.

The aptamers taught herein can be administered to a patient in a composition containing the aptamer or a salt thereof and a pharmaceutically acceptable carrier. For example, the aptamer can be combined with a water or alcohol containing media for administration. Similarly, the aptamer can be administered in tablet form together with a binder such as a sugar- or starch-based binder. Generally, speaking, the invention can be administered directly to a mammalian subject using any route known in the art, including e.g., by injection (e.g., intravenous, intraperitoneal, subcutaneous, intramuscular, or intradermal), inhalation, transdermal (topical) application, rectal administration, or oral administration. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed., 1989). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may also be coupled with soluble polymers as targetable drug carriers. Such polymers can include polyvinyl-pyrrolidone, pyran copolymer, polyhydroxypropylmethaciyl-amidephenol, polyhydroxy-ethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

All patents, patent applications, provisional applications, and publications referred to or cited herein, including those listed below, are incorporated by reference in their entirety, including all figures and tables, to the extent they are not inconsistent with the explicit teachings of this specification.

1. Shum K. T., Chan C., Leung C. M. & Tanner J. A. Identification of a DNA aptamer that inhibits sclerostin's antagonistic effect on Wnt signaling. *Biochem J*, 423, 501-510 (2011).
2. Goltzman, D., *Nat Rev Drug Discov* 1, 784-796. (2002).
3. Harada, S., and Rodan, G. A., *Nature* 423, 349-355. (2003).
4. Balemans, W., Ebeling, M., Patel, N., Van Hul, E., Olson, P., Dioszegi, M., Lacza, C., Wuyts, W., Van Den Ende, J., Willems, P., Paes-Alves, A. F., Hill, S., Bueno, M., Ramos, F. J., Tacconi, P., Dikkers, F. G., Stratakis, C., Lindpaintner, K., Vickery, B., Foernzler, D., and Van Hul, W., *Hum Mol Genet* 10, 537-543. (2001).
5. Brunkow, M. E., Gardner, J. C., Van Ness, J., Paeper, B. W., Kovacevich, B. R., Proll, S., Skonier, J. E., Zhao, L., Sabo, P. J., Fu, Y., Alisch, R. S., Gillett, L., Colbert, T., Tacconi, P., Galas, D., Hamersma, H., Beighton, P., and Mulligan, J., *Am J Hum Genet* 68, 577-589. (2001).
6. Hamersma, H., Gardner, J., and Beighton, P., *Clin Genet* 63, 192-197. (2003).
7. Li, X., Zhang, Y., Kang, H., Liu, W., Liu, P., Zhang, J., Harris, S. E., and Wu, D., *J Biol Chem* 280, 19883-19887. (2005).
8. Semenov, M., Tamai, K., and He, X., *J Biol Chem* 280, 26770-26775. (2005).
9. Boyden, L. M., Mao, J., Belsky, J., Mitzner, L., Farhi, A., Mitnick, M. A., Wu, D., Insogna, K., and Lifton, R. P., *N Engl J Med* 346, 1513-1521. (2002).
10. Gong, Y., Slee, R. B., Fukai, N., Rawadi, G., Roman-Roman, S., Reginato, A. M., Wang, H., Cundy, T., Glorieux, F. H., Lev, D., Zacharin, M., Oexle, K., Marcelino, J., Suwairi, W., Heeger, S., Sabatakos, G., Apte, S., Adkins, W. N., Allgrove, J., Arslan-Kirchner, M., Batch, J. A., Beighton, P., Black, G. C., Boles, R. G., Boon, L. M., Borrone, C., Brunner, H. G., Carle, G. F., Dallapiccola, B., De Paepe, A., Floege, B., Halfhide, M. L., Hall, B., Hennekam, R. C., Hirose, T., Jans, A., Juppner, H., Kim, C. A., Keppler-Noreuil, K., Kohlschuetter, A., LaCombe, D., Lambert, M., Lemyre, E., Letteboer, T., Peltonen, L., Ramesar, R. S., Romanengo, M., Somer, H., Steichen-Gersdorf, E., Steinmann, B., Sullivan, B., Superti-Furga, A., Swoboda, W., van den Boogaard, M. J., Van Hul, W., Vikkula, M., Votruba, M., Zabel, B., Garcia, T., Baron, R., Olsen, B. R., and Warman, M. L., *Cell* 107, 513-523. (2001).
11. Li, X., Ominsky, M. S., Warmington, K. S., Morony, S., Gong, J., Cao, J., Gao, Y., Shalhoub, V., Tipton, B., Haldankar, R., Chen, Q., Winters, A., Boone, T., Geng, Z., Niu, Q. T., Ke, H. Z., Kostenuik, P. J., Simonet, W. S., Lacey, D. L., and Paszty, C., *J Bone Miner Res* 24, 578-588. (2009).
12. Nimjee, S. M., Rusconi, C. P., and Sullenger, B. A., *Annu Rev Med* 56, 555-583. (2005).
13. Ellington, A. D., and Szostak, J. W., *Nature* 346, 818-822. (1990).
14. Tuerk, C., and Gold, L., *Science* 249, 505-510. (1990).
15. Que-Gewirth, N. S., and Sullenger, B. A., *Gene Ther* 14, 283-291. (2007).
16. Shum, K. T., and Tanner, J. A., *Chembiochem* 9, 3037-3045. (2008).
17. Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., and Higgins, D. G., *Bioinformatics* 23, 2947-2948. (2007).
18. Choi, M. Y., Chan, C. C., Chan, D., Luk, K. D., Cheah, K. S., and Tanner, J. A., *Biochem J* 423, 233-242. (2009).
19. Murphy, M. B., Fuller, S. T., Richardson, P. M., and Doyle, S. A., *Nucleic Acids Res* 31, e110. (2003).
20. Shafer, R. H., and Smirnov, I., *Biopolymers* 56, 209-227. (2000).
21. Veverka, V., Henry, A. J., Slocombe, P. M., Ventom, A., Mulloy, B., Muskett, F. W., Muzylak, M., Greenslade, K., Moore, A., Zhang, L., Gong, J., Qian, X., Paszty, C., Taylor, R. J., Robinson, M. K., and Carr, M. D., *J Biol Chem* 284, 10890-10900. (2009).
22. Rey, J. P., and Ellies, D. L., *Dev Dyn* 239, 102-114. (2010).

What is claimed is:

1. A composition comprising:
a DNA aptamer comprising an oligonucleotide having from about 14 to about 50 nucleotide repeat units and the sequence 5'-TTGCGCGTTAAT-TGGGGGGGTGGGTGGGTT-3' (SEQ ID NO: 3) (Scl 2) or a salt thereof,
wherein the aptamer inhibits sclerostin.

2. The composition of claim 1, wherein the aptamer has from about 20 to about 50 nucleotide repeat units.

3. The composition of claim 1, wherein the aptamer is conjugated with one or more selected from deoxythymidine nucleotide, inverted thymidine and polyethylene glycol.

4. The composition of claim 1, wherein the aptamer is an oligonucleotide having a backbone formed of deoxyribose-phosphate linkages.

5. The composition of claim 1, wherein the aptamer is an oligonucleotide having one or more deoxyribose-phosphate linkages stabilized by one or more selected from a thioester linkage and an amide linkage.

6. The composition of claim 1, wherein the aptamer has a parallel G-quadruplex structure.

7. An aptamer capable of binding sclerostin, the aptamer comprising an oligonucleotide having the sequence

```
                                              (SEQ ID NO: 3)
   5'-TTGCGCGTTAATTGGGGGGGTGGGTGGGTT-3'
   (Scl 2)
``` or a salt thereof, the aptamer comprising from about 14 to about 50 nucleotide repeat units.

8. The aptamer of claim 7, wherein the aptamer is conjugated with one or more selected from deoxythymidine nucleotide, inverted thymidine and polyethylene glycol.

9. The aptamer of claim 8, wherein the aptamer is conjugated at the 3' end with one or more selected from deoxythymidine nucleotide, inverted thymidine and polyethylene glycol.

10. The aptamer of claim 7, wherein the aptamer is an oligonucleotide having a backbone formed of deoxyribose-phosphate linkages.

11. The aptamer of claim 7, wherein the aptamer is an oligonucleotide having one or more deoxyribose-phosphate linkages stabilized by one or more selected from a thioester and an amide linkage.

12. The aptamer of claim 7, wherein the aptamer has a parallel G-quadruplex structure.

* * * * *